(12) United States Patent
Van Praag

(10) Patent No.: US 12,121,424 B2
(45) Date of Patent: Oct. 22, 2024

(54) SANITARY PAD WITH FOLD OUT ABRASION PROTECTION

(71) Applicant: Sarit Van Praag, Natanya (IL)

(72) Inventor: Sarit Van Praag, Natanya (IL)

( * ) Notice: Subject to any disclaimer, the term of this patent is extended or adjusted under 35 U.S.C. 154(b) by 428 days.

(21) Appl. No.: 17/621,708

(22) PCT Filed: Jun. 21, 2020

(86) PCT No.: PCT/IL2020/050690
§ 371 (c)(1),
(2) Date: Dec. 22, 2021

(87) PCT Pub. No.: WO2020/261260
PCT Pub. Date: Dec. 30, 2020

(65) Prior Publication Data
US 2022/0241120 A1    Aug. 4, 2022

Related U.S. Application Data

(60) Provisional application No. 62/866,620, filed on Jun. 26, 2019.

(51) Int. Cl.
| | | |
|---|---|---|
| *A61F 13/15* | (2006.01) | |
| *A61F 13/47* | (2006.01) | |
| *A61F 13/472* | (2006.01) | |
| *A61F 13/475* | (2006.01) | |
| *A61F 13/56* | (2006.01) | |

(52) U.S. Cl.
CPC .... *A61F 13/4704* (2013.01); *A61F 13/47218* (2013.01); *A61F 13/47236* (2013.01); *A61F 13/4758* (2013.01); *A61F 13/5616* (2013.01)

(58) Field of Classification Search
CPC ........ A61F 13/45; A61F 13/475; A61F 13/56; A61F 13/4704; A61F 13/47218; A61F 13/47236; A61F 13/4758; A61F 13/5616
See application file for complete search history.

(56) References Cited

U.S. PATENT DOCUMENTS

| | | |
|---|---|---|
| 2,688,328 A | 9/1954 | Marcus |
| 4,067,336 A | 1/1978 | Johnson |
| 4,804,380 A | 2/1989 | Lassen |
| 6,443,932 B1 | 9/2002 | Maggiulli |

(Continued)

FOREIGN PATENT DOCUMENTS

| | | |
|---|---|---|
| EP | 0302523 A2 | 2/1989 |
| EP | 0302523 B1 | 4/1994 |

(Continued)

*Primary Examiner* — Jacqueline F Stephens

(57) ABSTRACT

The current invention in some embodiments thereof relates to a sanitary pad which has a flat configuration for easy storage and transport and folds to form a 3D shape including a bulge for dividing between skin in a sensitive area. In some embodiments, in the bulge may be perpendicular to a flat portion of the pad. Optionally, the fin may have a triangular shape. For example, a menstrual pad may include an anterior flat area configured to lie against the vagina and/or absorb menstrual fluids and a posterior bulge configured to fit into an intergluteal cleft. For example, the bulge may have the form of a triangular fin. Optionally, the pad is reformed from the flat configuration to its 3D configuration by folding a posterior portion of the pad.

10 Claims, 10 Drawing Sheets

(56) References Cited

U.S. PATENT DOCUMENTS

| | | |
|---|---|---|
| 6,613,031 B2 | 9/2003 | Glasgow et al. |
| 7,504,552 B2 | 3/2009 | Tamura et al. |
| 7,670,324 B2 | 3/2010 | LaVon et al. |
| 10,376,424 B2 | 8/2019 | Park et al. |
| 2003/0135188 A1 | 7/2003 | Yoshimasa |
| 2005/0107762 A1 | 5/2005 | Ostrow |
| 2005/0267433 A1 | 12/2005 | Tanio et al. |
| 2008/0103474 A1 | 5/2008 | Luizzi |
| 2008/0312630 A1 | 12/2008 | Seo |
| 2009/0118691 A1 | 5/2009 | Rosenfeld |
| 2009/0287171 A1 | 11/2009 | Ito et al. |
| 2011/0257619 A1* | 10/2011 | Tosado ............... A61F 13/4758 604/385.16 |
| 2012/0035570 A1 | 2/2012 | Washington |
| 2012/0310202 A1 | 12/2012 | Wilson |
| 2014/0025028 A1 | 1/2014 | Stewart |
| 2015/0173969 A1 | 6/2015 | Goldsmith et al. |
| 2016/0296385 A1 | 10/2016 | Samuelsson |
| 2017/0224545 A1 | 8/2017 | Zilm |

FOREIGN PATENT DOCUMENTS

| | | |
|---|---|---|
| EP | 1395217 B1 | 2/2006 |
| KR | 20070028267 A | 3/2007 |

* cited by examiner

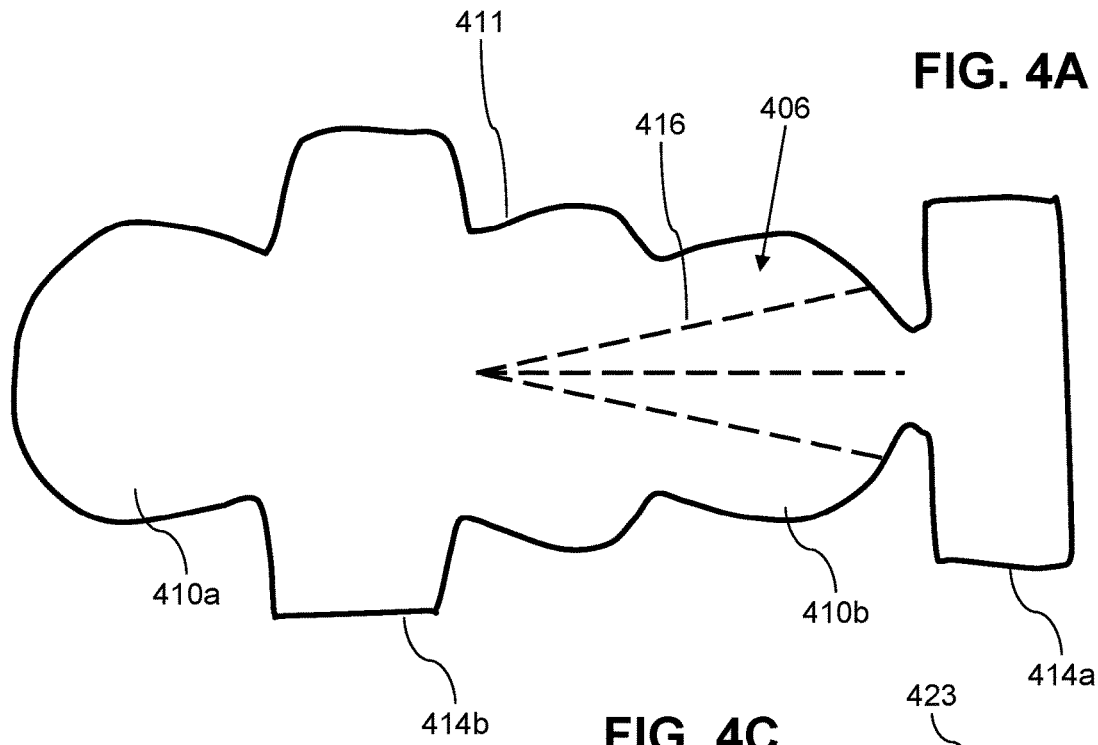
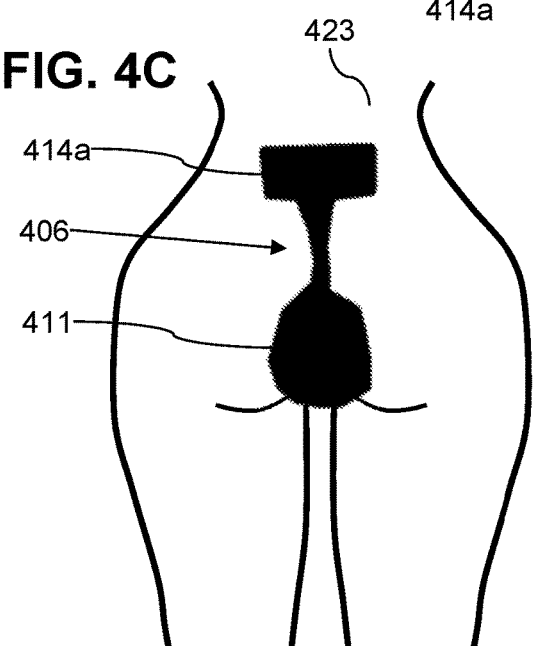
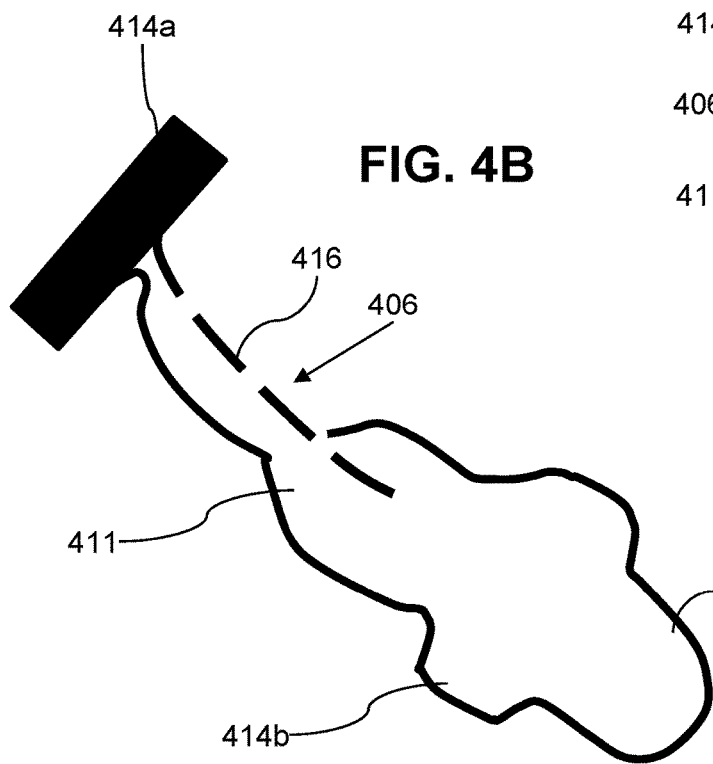

SANITARY PAD WITH FOLD OUT ABRASION PROTECTION

RELATED APPLICATION/S

This application claims the benefit of priority under 35 USC § 119(e) of U.S. Provisional Patent Application No. 62/866,620 filed 26 Jun. 2020, the contents of which are incorporated herein by reference in their entirety.

FIELD AND BACKGROUND OF THE INVENTION

The present invention, in some embodiments thereof, relates to a sanitary pad and, more particularly, but not exclusively, to a pad with abrasion protection.

U.S. Pat. No. 6,613,031 appears to disclose "A sanitary napkin having a front flap that adhesively attaches to the user's undergarment and a tail strip that extends rearwardly to reside in the user's intergluteal crevice. The pad thus fits more snugly against the body of the user. Further, because the strip provides improved body contact, similar protection is achieved with a smaller pad, thus providing a discretion."

US Patent Publication no. 20050267433 appears to disclose, that "A sanitary napkin includes a surface element that is formed of a liquid-permeable top sheet covering a liquid absorbent layer. The surface element is raised from the skin-side surface of a napkin body by an elastic force of an elastic member to form a protuberance having a front end and a rear end. The protuberance fits in the intergluteal cleft and prevents rearward leakage of menstrual blood."

US Patent Publication no. 20080312630 appears to disclose, "A sanitary pad auxiliary appendage (10) for separate attachment at the rear end (38) of a sanitary pad (100) so as to form an extension of said sanitary pad, said auxiliary appendage comprising a base portion (12) and a fin-like structure (14) extending at least a portion of the length of said base portion, said fin-like structure projecting upwardly from said base portion, said fin-like structure adapted to at least partially fill a crevice between the buttocks of a user so as to form a barrier between the thighs and buttocks of said user."

European Patent no. EP0302523 appears to disclose, "a three-dimensionally shaped, externally worn feminine protection device is formed which has been mechanically shaped by folding, molding or other forming techniques in such a way that it has a raised portion located within the back one-half to two-thirds of the device that functions to cause the pad to readily fit to and generally align itself within the inverted V-shaped regions of the woman's lower abdominal region, vulva, perineum and the anterior portion between the buttocks. The forward portion of the device of the invention generally is substantially flattened in use to cover externally the area of the pubic mons and the area exterior of the clitoris. The back portion of the device is formed in a peak like shape which readily adjusts to and molds to the inverted V-shape of the rear portion of the labia, the perineum and the forward portion of the area between the buttocks."

U.S. Pat. No. 7,504,552 appears to disclose, "an absorbent article including compressed grooves (11) and a rear flexible portion (16). The compressed grooves (11) where a liquid absorbent layer (4) is compressed and recessed from the side of a skin surface toward a garment surface are provided to extend in a longitudinal direction of the article so as to approach each other the nearest on a lateral reference line (Ox-Ox) of the article. The rear flexible portion (16) where the liquid absorbent layer (4) is recessed from the side of the garment surface toward the skin surface is provided to extend toward a rear end edge (1 d) from a starting point (16 a) that is located closer to the rear end edge (1 d) than the lateral reference line (Ox-Ox). At least a portion of the rear flexible portion (16) is located between the compressed grooves (11)."

U.S. patent Ser. No. 10/376,424 appears to disclose, "An absorbent article includes a base-structure and an elevatable structure known as a flat-back protection feature, that is capable of rising above the base-structure during article use. The flat-back protection feature utilizes either differences in material length compared with the length of the adjacent base-structure, or elastic materials, to maintain the feature elevation above the base-structure, while the article is in an extended condition. The flat-back protection feature extends into the intergluteal cleft of a wearer during use. Embossment features on the absorbent article are used to facilitate folding of the absorbent article, enhance the functionality of the protection feature, and/or improve the ease of manufacture."

SUMMARY OF THE INVENTION

According to an aspect of some embodiments of the invention, there is provided a hygienic pad including: a flat section; a 3D section projecting from the flat section and wherein the 3D section folds out from the flat section such that the pad can be stored in a flat configuration and folded to a 3D configuration before use.

According to some embodiments of the invention, the 3D section includes a triangular fin.

According to some embodiments of the invention, the 3D section includes three non-parallel folding lines.

According to some embodiments of the invention, 3D section is configured to fold out from the pad when the pad is bent around a crotch of a user.

According to some embodiments of the invention, the 3D section is configured to be folded manually by a user before use.

According to some embodiments of the invention, the 3D section is configured to fit between buttocks of a user.

According to some embodiments of the invention, the flat section includes two wide sections connected by a narrow section.

According to some embodiments of the invention, the 3D section includes a front face configured to contact a skin of a user and a back face including an adhesive to hold the 3D section folded and projecting from the flat section.

According to some embodiments of the invention, the 3D section includes two large wings configured to sit on inner thighs of a user.

According to some embodiments of the invention, the wings include an adhesive for attaching to a user.

According to some embodiments of the invention, the pad further includes: a wing configured for attaching to underwear of a user.

According to an aspect of some embodiments of the invention, there is provided a method of protecting skin of a user including: supplying a pad in a flat configuration; folding a 3D section of the pad to project from a flat section of the pad and placing the flat section of the pad onto skin of a user with the 3D section projecting between two moving portions of a body of the user.

According to some embodiments of the invention, the folding forms the 3D section into a triangular fin.

According to some embodiments of the invention, the folding is along three non-parallel folding lines.

According to some embodiments of the invention, the method further includes: bending the flat section around a crotch of a user and wherein the folding results from the bending.

According to some embodiments of the invention, folding is manual by a user before use.

According to some embodiments of the invention, the method further includes: fitting the 3D section between buttocks of a user.

According to some embodiments of the invention, the flat section includes two wide sections connected by a narrow section, the method further including: retaining the narrow section in a crotch of the user.

According to some embodiments of the invention, the 3D section includes a front face configured to contact a skin of a user and a back face, the method further including: adhering the back face of the 3D section to retain the 3D section projecting from the flat section.

According to some embodiments of the invention, the method further includes: positioning the 3D section on inner thighs of the user.

According to some embodiments of the invention, the method further includes: adhering the 3D section to inner thighs of the user.

According to some embodiments of the invention, the method further includes: a wing configured for attaching to underwear of a user.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWING(S)

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 4A is a schematic illustration of a pad in a flat configuration in accordance with an embodiment of the current invention;

FIG. 4B is a schematic illustration of a pad in a 3D configuration in accordance with an embodiment of the current invention;

FIG. 4C is a schematic illustration of a pad being worn in accordance with an embodiment of the current invention;

DESCRIPTION OF SPECIFIC EMBODIMENTS OF THE INVENTION

Figure 1:
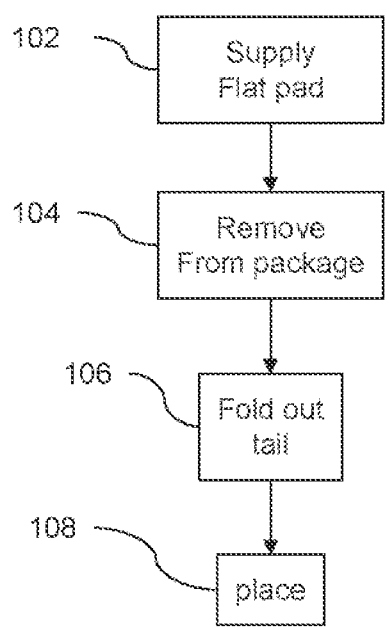
FIG. 1 is a flow chart illustrating placement of a protective pad in accordance with an embodiment of the current invention.

The present invention, in some embodiments thereof, relates to a sanitary pad and, more particularly, but not exclusively, to a pad with abrasion protection.

Overview

The current invention in some embodiments thereof relates to a sanitary pad which has a flat configuration for easy storage and transport and folds to form a 3D shape including a bulge for dividing between skin in a sensitive area. In some embodiments, the bulge may be perpendicular to a flat portion of the pad. Optionally, the fin may have a triangular shape. For example, a menstrual pad may include an anterior flat area configured to lie against the vagina and/or absorb menstrual fluids and a posterior bulge configured to fit into an intergluteal cleft. For example, the bulge may have the form of a triangular fin. Optionally, the pad is reformed from the flat configuration to its 3D configuration by folding a posterior portion of the pad. The current invention in some embodiments thereof relates to a hygienic pad.

For example, the pad may have the form of a bandage and/or an absorbent pad. Such pads may be used by women, men, athletes, infants, the infirm and/or elderly. In some embodiments, the pad may include a flat section (the flat section may also be slightly curved) that fits against the skin and/or absorbs bodily secretions (e.g. defecation, anal secretions, urine, menstrual flow etc.). Additionally or alternatively, the pad may include a 3D section (for example, a fold out and/or bulge) that divides between moving sections of the skin to reduce friction, rubbing, chaffing and the like. For example, a 3D section of a menstrual pad may include a triangular section similar to an airplane tail. The 3D section optionally goes in between the two parts of the buttocks. Optionally, an attacher (for example tape) is included on the tail. For example, the tape may adhere to the body, thus holding the tail in place. Additionally or alternatively, there may be wings that hold the pad to the body and/or underwear of the user and intervein between thighs of a user.

Embodiments of the invention disclose a pad with a diagonal triangular bulge. For example, the bulge may be shaped like an aircraft tail, with a straight or semicircular diagonal line. Optionally the bulge is located on the back section of the pad. For example, the shape of the bulge may be configured for insertion between butt cheeks and/or for separating the butt-cheeks.

The pad may be without wings and/or with small wings to be affixed to the underwear and/or with large wings, to affix to the inner part of the thigh. The size of the wings may range, for example, between 15 cm to 17 cm and/or between 10 to 15 cm and/or between 5 to 10 cm and/or between 1 to 5 cm and/or between 17 to 25 cm. Optionally, glue affixes the pad to the user and/or clothes. The glue that affixes the pad can be of a single-use or reusable. The wings may be made of material that adheres to the body with a soft feel so that the friction between the two thighs is natural, smooth and/or pleasant. The pad that affixes the inner part of the thigh may be with or without the tail.

In some embodiments the pad includes only a front part for protecting the body but yet provides ventilation. The length of the inner part may be for example range between 8 to 12 cm and/or between 4 to 8 cm and/or between 1 to 4 cm and/or between 12 to 15 cm and/or between 15 to 20 cm. The length of the tail may range, for example between 12 to 17 cm and/or between 8 to 12 cm and/or between 4 to 8 cm and/or between 1 to 4 cm and/or between 17 to 25 cm.

One problem solved in some embodiments described by the present disclosure is how to avoid friction between two body parts, for example, the butt-cheeks and/or thighs. The pad may also protect from moisture, for example, in a closed, perspiring area with body secretions. Optionally, the pad protects from friction rubbing that may lead to discomfort, sores, infections, and/or chafe, causing. Such irritation can be a source of a great deal of suffering to the extent of limiting movement.

In some embodiments, such problems are inhibited by a pad with a tail (the lengthwise upward bulge on the back section). The pad is optionally worn between the butt-cheeks to form a physical partition that prevents the friction and/or rubbing of the skin and/or absorbs the perspiration and/or body secretions, thereby preventing infections, sores, chafe and/or discomfort in advance.

The pad may be made of any material, for example, materials used to manufacture absorbent products. The materials can be natural reusable or single-use. The pad can have dimensions to cover the entire underpants or the back section only.

The pad can have the option of a back and/or upper adhesive strip or only underneath, so that it can be used by women, men, athletes, babies and/or senior citizens.

The pad may be suitable for daily use.

Specific Embodiments

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

Referring now to the drawings:

FIG. 1 is a flow chart illustrating placement of a protective pad in accordance with an embodiment of the current invention. In some embodiments, a pad may be supplied 102 in a flat configuration. For example, the pad may be packaged in the flat configuration in a protective package and/or in a sanitary pouch. A pile of flat pads may be sold in a bag and/or box and/or wrapped in plastic. Alternatively or additionally, each pad may be individually wrapped. Optionally in the flat configuration, the pad may be folded into layers. For example, in the flat configuration, the height of the pad may be less than 1 cm and/or less than 2 cm and/or less than 4 cm. In some embodiment, the flat pad is removed 104 its packaging and/or folded 106 to a 3D configuration. For example, in the 3D configuration, a bulge may protrude from a flat area and/or be perpendicular to the flat area. For example, a portion of the pad may be folded 106 along intersecting lines so to form a triangular fin. Optionally, a retainer (for example tape and/or a connector and/or an elastic element) holds the pad in its 3D configuration.

Optionally, the pad may be placed 108 against skin in its 3D form. For example, a flat area may cover a body part and/or the bulge may separate between body parts. For example, a flat part may cover a vaginal area of a woman and/or absorb vaginal discharge. For example, a bulge in the pad may fit into an intergluteal cleft of a woman to protect the intergluteal cleft from menstrual fluids and/or from abrasion.

Figure 2:
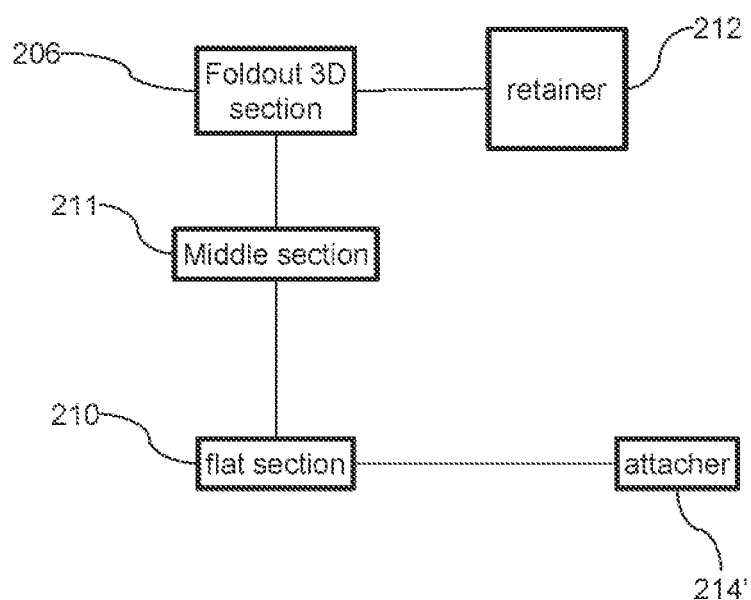
FIG. 2 is a block diagram of a pad in accordance with an embodiment of the current invention.

FIG. 2 is a block diagram of a pad in accordance with an embodiment of the current invention. In some embodiments, a pad may include a flat section 210 and/or a bulge. For example, the bulge may include a triangular fold out 206. Optionally a retainer 212 (for example, including adhesive and/or a clip and/or a tab) may retain the folded section in its 3D configuration. In some embodiments, a pad may include an attacher 214. For example, the attacher 214 may include wings and/or adhesive. Optionally, attacher 214 attaches the pad to the skin of a wearer. Alternatively or additionally, the attacher 214 attaches the pad to the clothing of a user. For example, a feminine sanitary pad may include a flat front section 210 that covers the vagina and/or absorbs menstrual fluids. Additionally or alternatively, the pad may include a middle section 211 that is bent upwards across the crotch and a rear 3D section that is positioned next to the intergluteal cleft when the middle section 211 is bent around the crotch. Optionally there is a fold out 206 in the middle of the 3D rear section and/or the geometry of the pad is configured such that bending the front section and/or middle crotch section around the body of the wearer cause the rear 3D section to fold around a folding line forming a 3D foldout 206 that fits into the intergluteal cleft and/or inhibits menstrual fluids from entering and/or inhibits chaffing.

Figure 3:
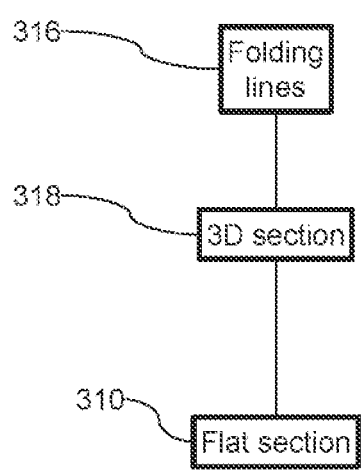
FIG. 3 is a block diagram of a pad in accordance with an embodiment of the current invention.

FIG. 3 is a block diagram of a pad in accordance with an embodiment of the current invention. Optionally, a 3D section 318 of the pad may include a fold out bulge. For example, the bulge may be formed like a triangular fin by folding the pad along folding lines 316. For example, three folding lines 316 may intersect at a point to form a triangular fold out, like an airplane tail. Optionally, the fold out lines include areas where the pad is thin and/or a scored area and/or a prefolded section. The pad optionally includes a flat section 310.

FIG. 4A is a schematic illustration of a pad in accordance with an embodiment of the current invention. In some embodiments, a pad may include a flat section 410a, 410b and/or a bulge. For example, the bulge may include a triangular fold out 406. Optionally a retainer (for example an adhesive on the back of a fold out fin that holds the backs of the folded sections 406 together) may retain the folded section 406 in its 3D configuration. In some embodiments, a pad may include an attacher 414a, 414b. For example, the attacher 414a may include an adhesive (e.g. tape and/or a sticker). Optionally the adhesive may be on one side of the attacher 414a (e.g. on the front for connecting to the body of the wearer and/or on the back to attach to the underwear of the wearer). Alternatively or additionally, the adhesive 414a may be on both sides of the attacher two side (underwear/body). Alternatively or additionally, attacher 414a may include tab that attaches to the back of a wearer and/or to a top rear portion of their underwear (for example by folding over the top of the underwear and/or by adhering). For example, the attacher 414b may include wings that attach to the front of a wearer and/or to a rear portion of their underwear. For example, a feminine sanitary pad may include a flat front section 410a that covers the vagina and/or absorbs menstrual fluids. Additionally or alternatively, the pad may include a middle section 411 that is bent upwards across the crotch and a rear 3D section that is positioned next to the intergluteal cleft when the middle section 411 is bent around the crotch. Optionally there is a fold out 406 in the middle of the 3D rear section and/or the geometry of the pad is configured such that bending the front section 410a and/or middle crotch section 411 around the body of the wearer cause the rear 3D section 406 to fold around a folding lines 416 forming a 3D section 406 the fits into the intergluteal cleft and/or inhibits menstrual fluids from entering and/or inhibits chaffing. Alternatively or additionally, a user may manually fold the pad along folding lines 416 before using the pad.

FIG. 4B is a schematic illustration of a pad in a 3D configuration in accordance with an embodiment of the current invention. The flat configuration of the pad is optionally folded along lines 416 and/or bent around the crotch to form a 3D configuration.

FIG. 4C is a schematic illustration of a pad being worn on the back of an abdomen 423 in accordance with an embodiment of the current invention. Optionally in the 3D configuration, the triangular fold out 406 leaves a fin section fitting in the intergluteal cleft and a flat section around the sides of the cleft.

Figure 5A:
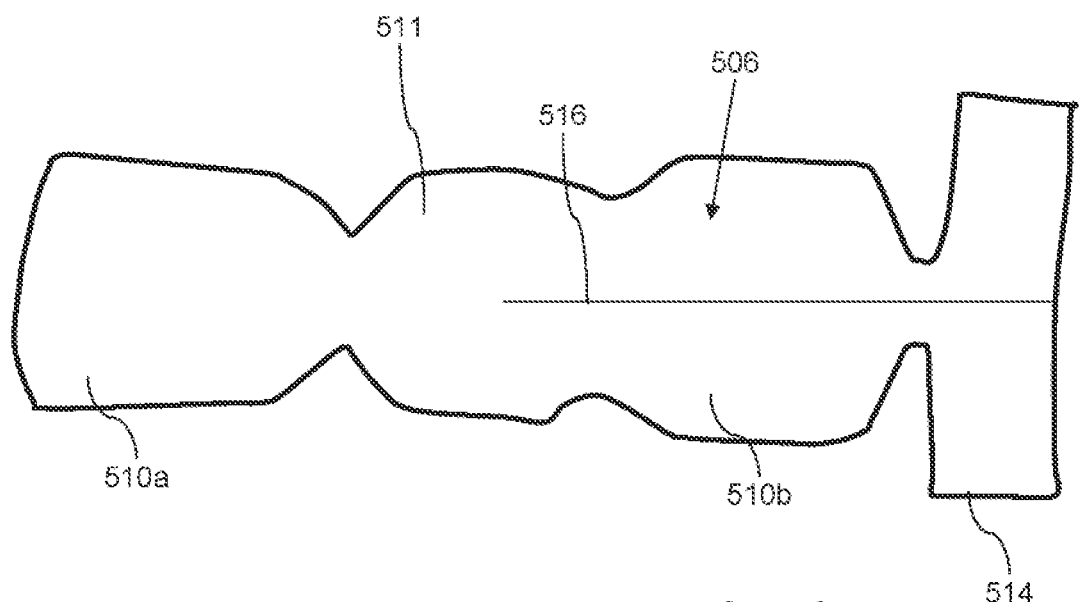
FIG. 5A is a schematic illustration of a pad in a flat configuration in accordance with an embodiment of the current invention.

FIG. 5A is a schematic illustration of a pad in accordance with an embodiment of the current invention. In some embodiments, a pad may include a flat section 510a, 510b and/or a bulge. For example, a 3D section 506 may include a central fold 516. Optionally a retainer (for example an adhesive on the back of a fold out fin that holds the backs of the 3D sections 506 together) may retain the folded section 506 in its 3D configuration. In some embodiments, a pad may include an attacher 414a. For example, the attacher 414a may include adhesive on the front and/or band and/or a tab that attaches to the back of a wearer and/or to a top rear portion of their underwear. For example, a feminine sanitary pad may include a flat front section 510a that covers the vagina and/or absorbs menstrual fluids. Additionally or alternatively, the pad may include a middle section 511 that is bent upwards across the crotch and a rear 3D section that is positioned next to the intergluteal cleft when the middle section 511 is bent around the crotch. Optionally there is a fold out 506 in the middle of the 3D rear section and/or the geometry of the pad is configured such that bending the front section 510a and/or middle crotch section 511 around the body of the wearer cause the rear 3D section 506 to fold around a folding line 516 forming a 3D section 506 the fits into the intergluteal cleft and/or inhibits menstrual fluids from entering and/or inhibits chaffing.

Figure 5B:
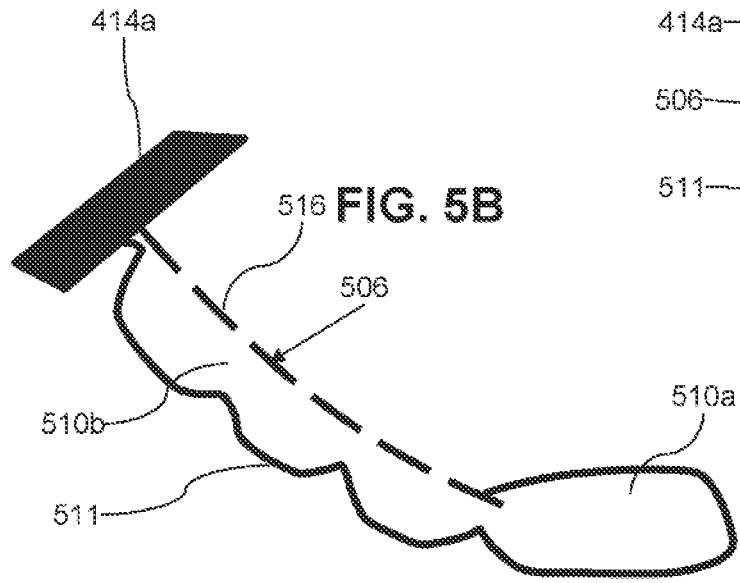
FIG. 5B is a schematic illustration of a pad in a 3D configuration in accordance with an embodiment of the current invention.

FIG. 5B is a schematic illustration of a pad in a 3D configuration in accordance with an embodiment of the current invention. The flat configuration of the pad is optionally folded along lines 516 and/or bent around the crotch to form a 3D configuration.

Figure 5C:
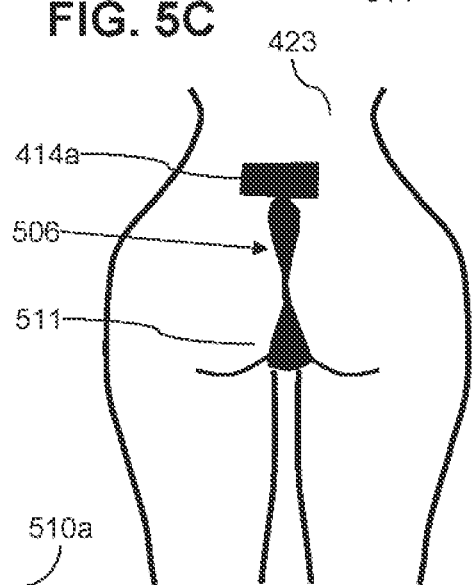
FIG. 5C is a schematic illustration of a pad being worn in accordance with an embodiment of the current invention.

FIG. 5C is a schematic illustration of a pad being worn in accordance with an embodiment of the current invention. Optionally, in the 3D configuration, the fold out 506 leaves a fin section fitting in the intergluteal cleft.

Figure 6A:
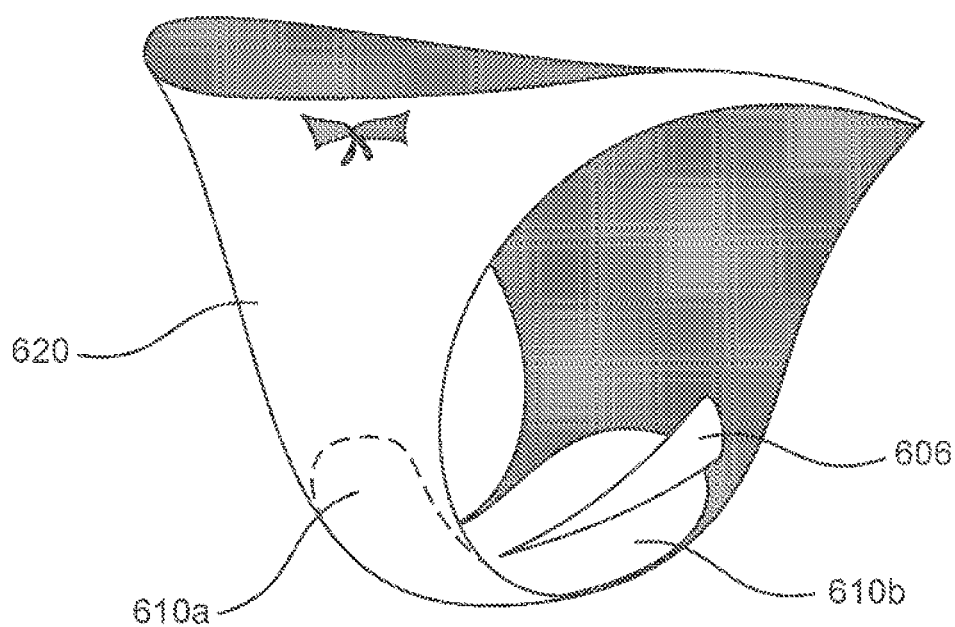
FIG. 6A is a schematic illustration of a pad in a pair of underpants in accordance with an embodiment of the current invention.

FIG. 6A is a schematic illustration of a pad 601 in a pair of underpants in accordance with an embodiment of the current invention. In some embodiments, a rear section 610b of the pad 601 sits on and/or attaches to a rear portion of underwear 620. Additionally or alternatively, a front section 610a of the pad 601 sits on and/or is attached to a front portion of the underwear 620. Optionally a 3D section 606 may include a folded section integral to of the pad. Alternatively or additionally, the 3D section 606 may be affixed to the pad and/or imprinted thereon. Alternatively or additionally, the 3D section 606 and/or the pad 601 may be affixed to the underwear and/or imprinted thereon. In some embodiments, the 3D sections 606 points inwards. For example, a low portion of the 3D section may bulge and/or point inward at or just behind and/or just in front of the crotch of the underwear. Optionally the 3D section becomes higher, rising diagonally to a height of few cm (e.g. between 2 to 5 cm and/or between 0.5 to 2 cm and/or between 5 to 10 cm) as it rises up the rear section of the underwear. For example, the 3D section may be shaped like the tail of an aircraft and/or curve upwards and/or curve back downward at an upper rear portion of the underwear. In some embodiments, the tail may protrudes beyond the back edge of the pad for example between 0 to 2 cm and/or between 2 to 8 cm and/or between 8 to 12 cm and/or between 12 to 20 cm. Optionally the length of the tail may be changed depending of the size of the pad (e.g. longer for a longer pad). Alternatively or additionally, the 3D section not protrude behind the pad.

Figure 6B:
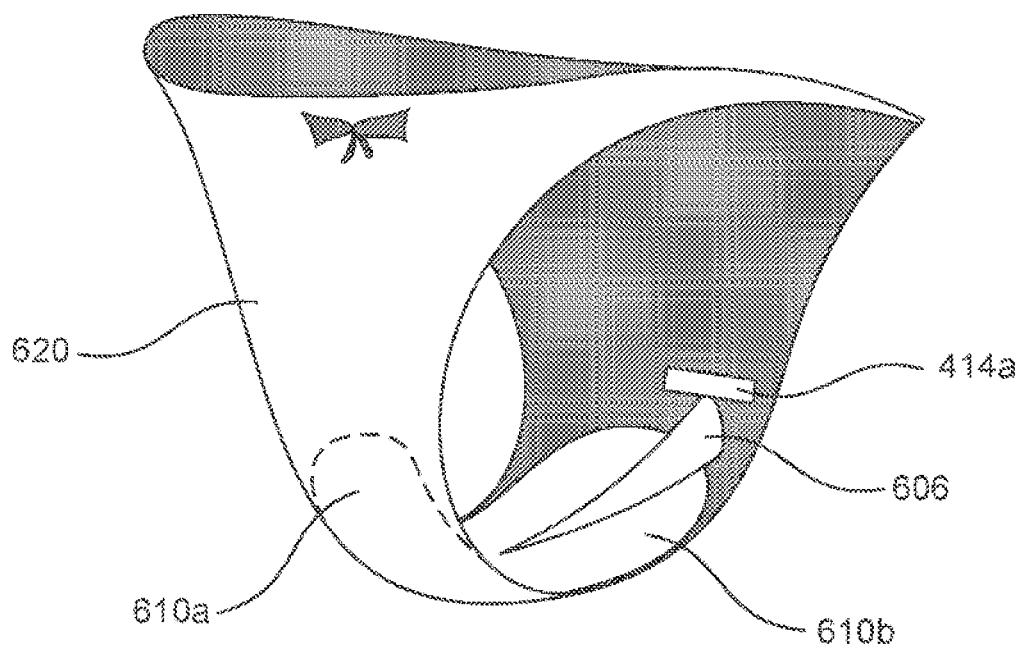
FIG. 6B is a schematic illustration of a pad with a rear attacher in a pair of underpants in accordance with an embodiment of the current invention.

FIG. 6B is a schematic illustration of a pad with an attacher 414a in a pair of underpants in accordance with an embodiment of the current invention.

Figure 7A:
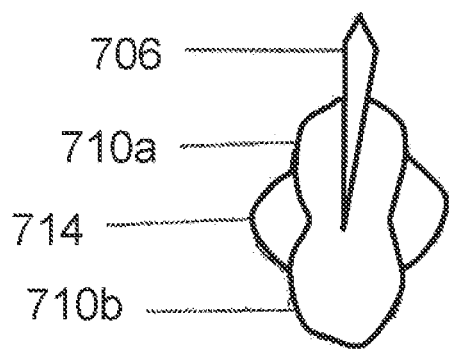
FIG. 7A is a schematic top and side view illustration of a pad with wings in accordance with an embodiment of the current invention.

FIG. 7A is a schematic top and side view illustration of a pad with wings in accordance with an embodiment of the current invention.

Figure 7B:
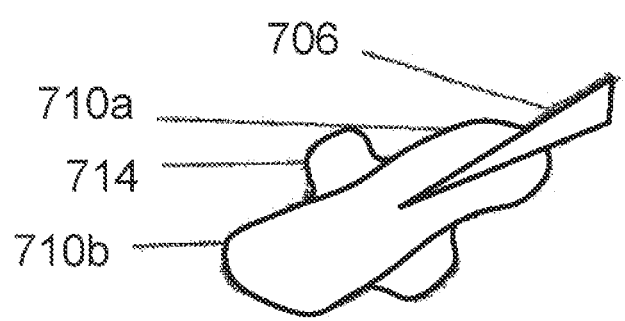
FIG. 7B is a schematic side view illustration of a pad with wings in accordance with an embodiment of the current invention.

FIG. 7B are schematic side view illustration of a pad with wings in accordance with an embodiment of the current invention. In some embodiments, a pad may include one or more flat sections 710a, 710b and/or a 3D section 706 and/or an attacher 714. For example, flat sections 710a, 710b may be configured for absorbing fluids and/or protecting a skin surface. For example, a feminine pad may have a front absorbent flat section 710b and/or a rear absorbent flat section 710a. Optionally the front section 710b may be more absorbent than the back section 710b. Optionally, an attacher 714 may include wings for attachment to underwear. Optionally, the 3D section 706 may include a triangular fold out and/or a tail. In some embodiments, the pad is supplied with the 3D section 706 folded flat.

In some embodiments, a pad is configured for use during a menstrual period. Alternatively or additionally, the pad suitable for absorbing other secretions and/or incontinence. Optionally, on the back flat section 710a of the bandage a 3D section 706 folds into tail that fits between two parts of the buttocks and/or the rear of the 3D section 706 may reach an upper end in the tailbone area on the back of the user. Optionally, the 3D section 706 includes tape that attaches the pad to the body of the user. In some embodiments, the pad has the form like a plane with an elevated 3D tail and/or wings.

In some embodiments, a smaller and/or narrower pad may be configured for daily use (e.g. when there is no menstrual flow). For example, the pad may prevent rubbing between the two parts of the buttocks and/or absorb sweat and/or absorb various minor secretions. For example, the pad may give a feeling of dryness and cleanliness throughout the day. For example, the pad may include a narrow front section 710b that dresses on the front part of the vulva. Optionally the pad is attached to the bottom of the user and/or his/her underwear with attachers 714. A rear section 710a optionally includes folds that form a long tail that fits between the two parts of the buttocks.

Figure 7C:
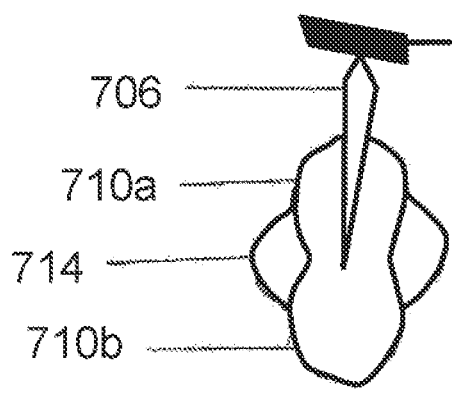
FIG. 7C is a schematic top and side view illustration of a pad with wings and a rear attacher in accordance with an embodiment of the current invention.

FIG. 7C is a schematic top and side view illustration of a pad with wings (attacher 714) and a rear attacher 414b in accordance with an embodiment of the current invention.

Figure 7D:
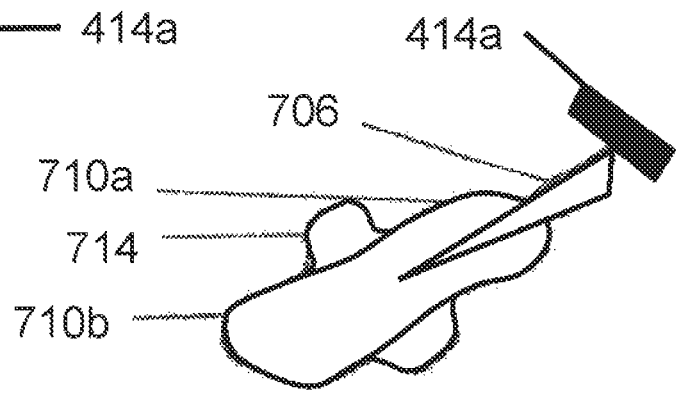
FIG. 7D is a schematic side view illustration of a pad with wings and a rear attacher in accordance with an embodiment of the current invention.

FIG. 7D is a schematic side view illustration of a pad with wings (attacher 714) and a rear attacher 414a in accordance with an embodiment of the current invention.

Figure 8A:
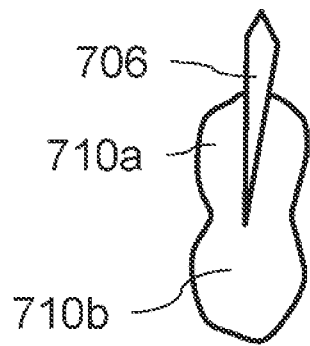
FIG. 8A is a schematic top view illustration of a pad without wings in accordance with an embodiment of the current invention.

FIG. 8A is a schematic top view illustration of a pad without wings in accordance with an embodiment of the current invention.

Figure 8B:
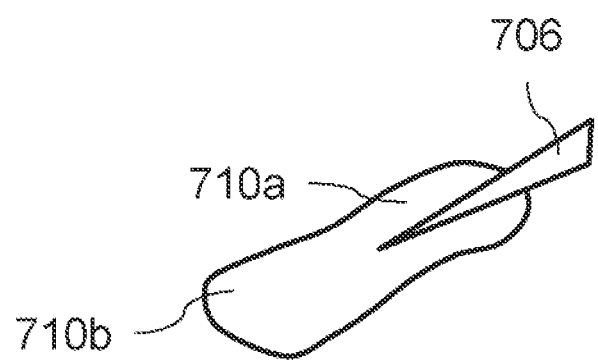
FIG. 8B is a schematic side view illustration of a pad without wings in accordance with an embodiment of the current invention.

FIG. 8B is a schematic side view illustration of a pad without wings in accordance with an embodiment of the current invention. Optionally, the pad has a contoured and/or hourglass shape with a narrow section between the front flat section 710b and the rear flat section 710a. For example, the narrow section of the pad may fit in the crotch and/or be held by snug fitting underpants to keep the pad from moving about. A wingless pad may be thick or thin (for example for menstrual and/or non menstrual time). Optionally, the pad may include a 3D section 706 and/or any of the features of the winged pads of FIGS. 7A and 7B as described above.

Figure 8C:
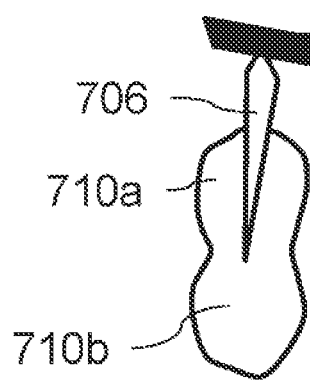
FIG. 8C is a schematic top and side view illustration of a pad without wings and with a rear attacher in accordance with an embodiment of the current invention.

FIG. 8C is a schematic top and side view illustration of a pad without wings and with a rear attacher 414a in accordance with an embodiment of the current invention.

Figure 8D:
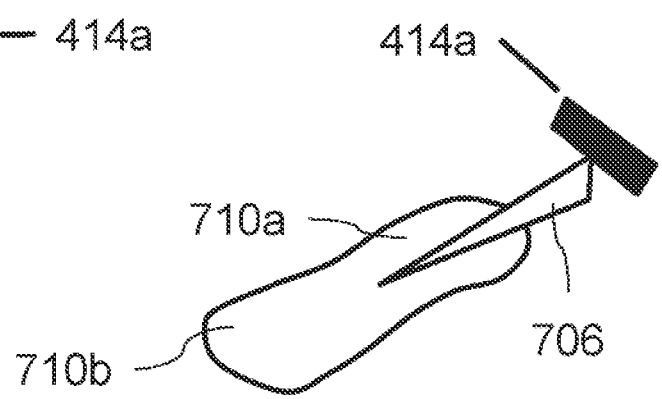
FIG. 8D is a schematic side view illustration of a pad without wings and with a rear attacher in accordance with an embodiment of the current invention.

FIG. 8D is a schematic side view illustration of a pad without wings and with a rear attacher 414a in accordance with an embodiment of the current invention.

Figure 9A:
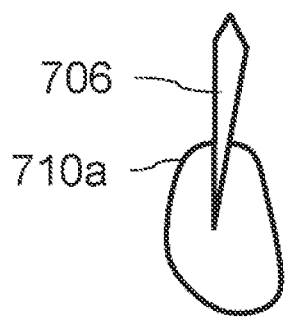
FIG. 9A is a schematic top view illustration of a pad without wings in accordance with an embodiment of the current invention.

FIG. 9A is a schematic top view illustration of a pad without wings in accordance with an embodiment of the current invention.

Figure 9B:
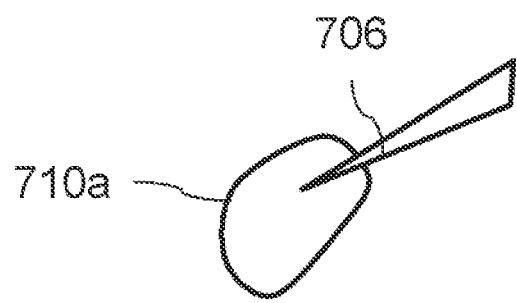
FIG. 9B is a schematic side view illustration of a pad without wings in accordance with an embodiment of the current invention.

FIG. 9B is a schematic side view illustration of a pad without wings in accordance with an embodiment of the current invention. Optionally, the pad has a one front flat section 710b. The pad may be held by snug fitting underpants to keep the pad from moving about. A wingless pad may be thick or thin (for example for menstrual and/or non menstrual time). Optionally, the pad may include a 3D section 706 and/or any of the features of the winged pads of FIGS. 7A and 7B as described above.

Figure 9C:
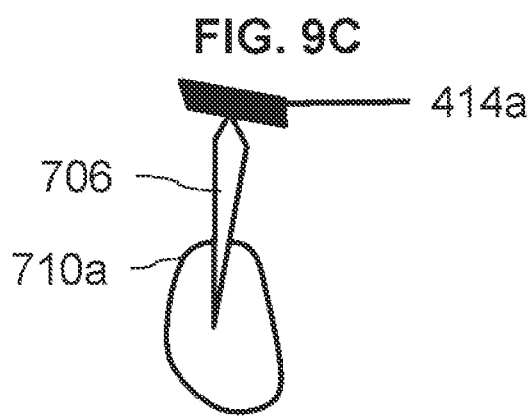
FIG. 9C is a schematic top and side view illustration of a pad without wings and with a rear attacher in accordance with an embodiment of the current invention.
Figure 9D:
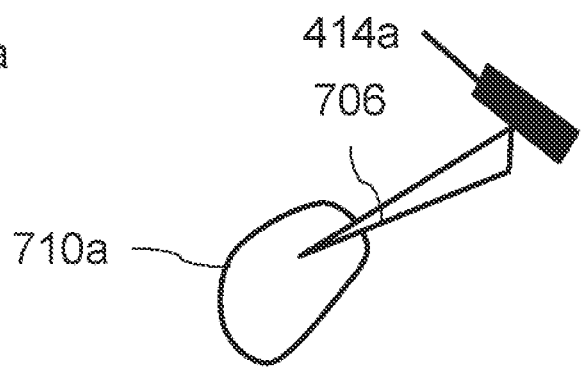
FIG. 9D is a schematic side view illustration of a pad without wings and with a rear attacher in accordance with an embodiment of the current invention.
Figure 10A:
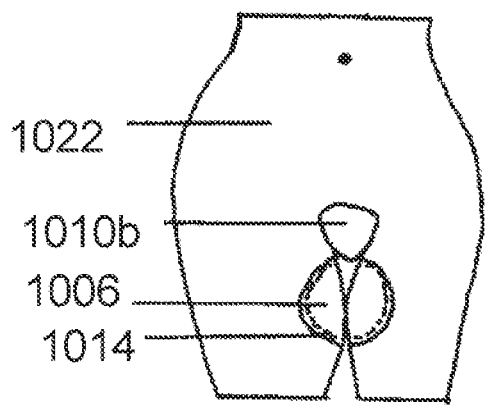
FIG. 10A is a front view of an abdomen of a person wearing a pad with large wings in accordance with an embodiment of the current invention.

FIG. 9C is a schematic top and side view illustration of a pad without wings and with a rear attacher 414a in accordance with an embodiment of the current invention;

FIG. 9D is a schematic side view illustration of a pad without wings and with a rear attacher 414a in accordance with an embodiment of the current invention;

FIG. 10A is a front view of an abdomen 1022 of a person wearing a pad with large wings in accordance with an embodiment of the current invention.

Figure 10B:
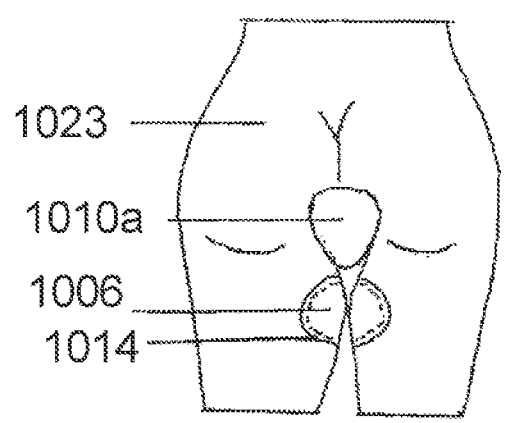
FIG. 10B is a back view of an abdomen of a person wearing the pad with large wings in accordance with an embodiment of the current invention.

FIG. 10B is a back view of an abdomen 1023 of a person wearing the pad of FIG. 10A with large wings in accordance with an embodiment of the current invention. Optionally the pad includes a front flat section 1010b, a rear flat section 1010a and/or a 3D section 1006, for example including wings configured to fold down and cover the inner thighs of a user. Optionally, the wings include an adhesive strip 1014 holding the wings to the thighs and/or holding the pad to the user. Optionally a pad may include 3D wings to prevent rubbing between the thighs and/or two parts of the buttocks. Such a pad may be configured for daily use or for use during the menstrual cycle (for example the flat portion of the pad may be larger, thicker and/or more absorbent for menstrual user). For example, the wings may range between 15 to 30 cm wide and/or between 5 to 15 cm and/or between 1 to 5 cm and/or between 30 to 60 cm wide. In some embodiments, the wings may include a rubber band and/or adhesive that embraces the hips and/or the thighs and/or sticks to them. For example, the large wings may prevent friction between the legs and/or the the inner thighs and/or may facilitate a woman walking comfortably without a need to wear tights under the dress.

Figure 10C:
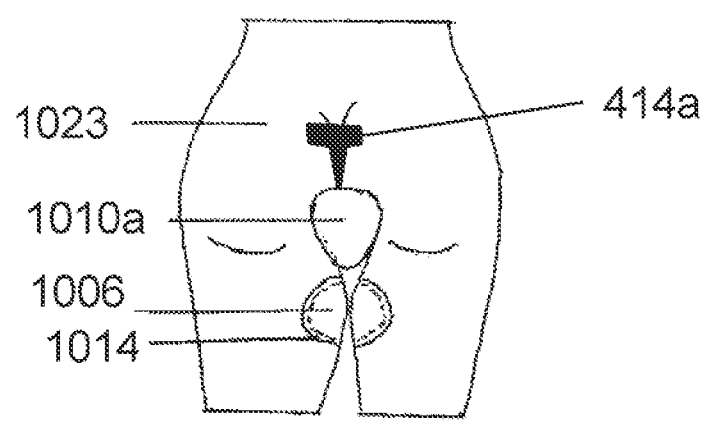
FIG. 10C is a back view of an abdomen of a person wearing the pad with large wings and a rear attacher in accordance with an embodiment of the current invention.

FIG. 10C is a back view of an abdomen 1023 of a person wearing the pad with large wings and a rear attacher 414a in accordance with an embodiment of the current invention.

Figure 11A:
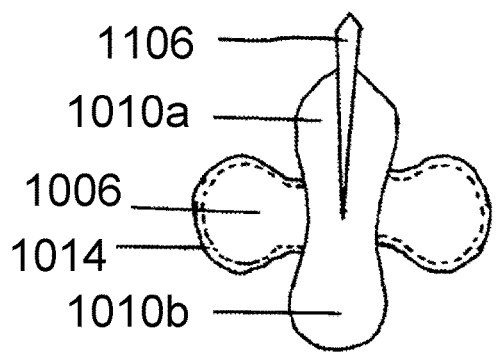
FIG. 11A is a top view illustration of a pad with two fold out 3D portions, large wings and/or a 3D cut fold out in accordance with an embodiment of the current invention.

FIG. 11A is a top view illustration of pad as in FIGS. 10A and/or 10B with two fold out 3D portions, large wings 3D section 1006 and/or a 3D cut fold out 1106.

Figure 11B:
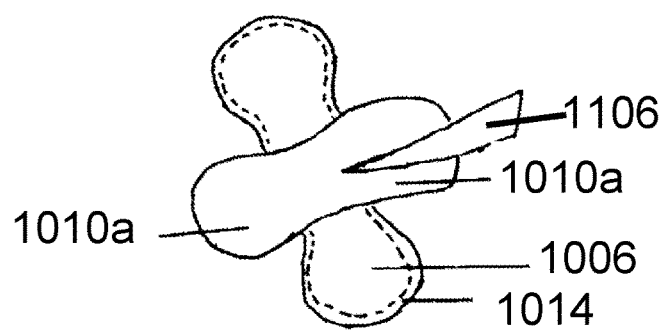
FIG. 11B is a side view illustration of a pad with two fold out 3D portions, large wings and/or a 3D cut fold out in accordance with an embodiment of the current invention.

FIG. 11B is a side view illustration of pad as in FIGS. 10A and/or 10B with two fold out 3D portions, large wings 3D section 1006 and/or a 3D cut fold out 1106. For example, wings 3D section 1006 may be configured to fold out and/or protect the inner thighs of a user and/or the tail fold out 1106 may be configured to fold out and/or prevent chaffing in between the buttocks.

Figure 11C:
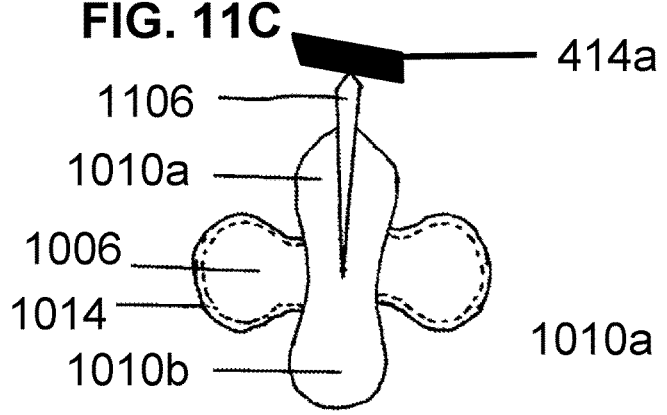
FIG. 11C is a top view illustration of a pad with two fold out 3D portions, large wings and/or a 3D cut fold out and/or a rear attacher in accordance with an embodiment of the current invention.

FIG. 11C is a top view illustration of a pad with two large wings 3D section 1006 and/or a 3D fold out 1106 and/or a rear attacher 414a in accordance with an embodiment of the current invention.

Figure 11D:
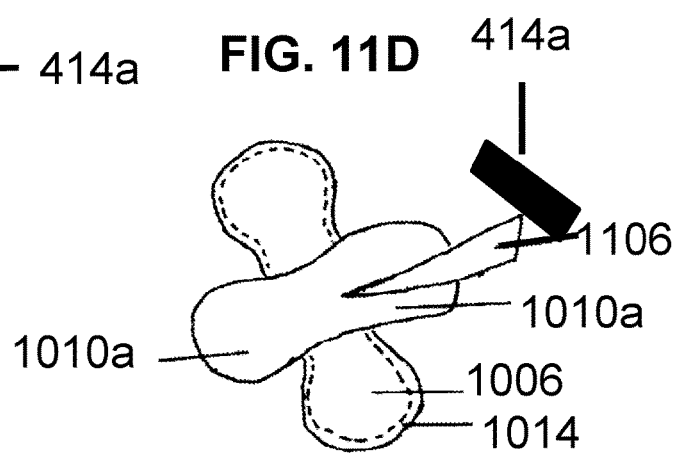
FIG. 11D is a side view illustration of a pad with two fold out 3D portions, large wings and/or a 3D cut fold out and/or a rear attacher in accordance with an embodiment of the current invention.

FIG. 11D is a side view illustration of a pad with two wing 3D sections 1006, large wings and/or a 3D fold 1106 out and/or a rear attacher 414a in accordance with an embodiment of the current invention.

Figure 12:
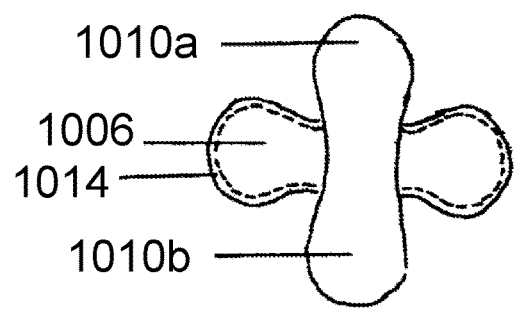
FIG. 12 is a top view illustration of a pad with large wings in accordance with an embodiment of the current invention.

FIG. 12 is a top view illustration of pad as in FIGS. 10A and/or 10B with large wings 1006. For example, wings 1006 may be configured to fold out and/or protect the inner thighs of a user.

It is expected that during the life of a patent maturing from this application many relevant technologies will be developed and the scope of the terms are intended to include all such new technologies a priori.

As used herein the term "about" refers to ±10% The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. When multiple ranges are listed for a single variable, a combination of the ranges is also included (for example the ranges from 1 to 2 and/or from 2 to 4 also includes the combined range from 1 to 4).

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

What is claimed is:

1. A method of protecting skin of a user comprising:
   supplying a pad in a flat configuration;
   bending a flat section around a crotch of the user;
   folding a 3D section of the pad to project from said flat section of the pad and placing the flat section of the pad onto skin of the user with said 3D section projecting between two moving portions of a body of the user,
   wherein the folding forms the 3D section into a triangular fin,
   wherein said folding is along three non-parallel folding lines and
   wherein said folding results from said bending.

2. The method of claim 1, wherein folding is manual by the user before use.

3. The method of claim 1, further comprising:
   fitting said 3D section between buttocks of the user.

4. The method of claim 1, wherein said flat section includes two wide sections connected by a narrow section, the method further comprising:
   retaining said narrow section in a crotch of the user.

5. The method of claim 1, wherein said 3D section includes a front face configured to contact a skin of the user and a back face, the method further comprising:
   adhering the back face of said 3D section to retain the 3D section projecting from said flat section.

6. The method of claim 1, further comprising:
   positioning said 3D section on inner thighs of the user.

7. The method of claim 6, further comprising:
   adhering said 3D section to inner thighs of the user.

8. The method of claim 1, further comprising:
   a wing configured for attaching to underwear of the user.

9. The method of claim 1, further comprising attaching adhesive tab extending from the 3D section configured to at least one of a back of a wearer and a top rear portion of their underwear of the wearer to hold the 3D section between buttocks of the user.

10. The method of claim 9, wherein said tab has a T shape.

* * * * *